United States Patent
Shatalov et al.

(10) Patent No.: US 11,027,319 B2
(45) Date of Patent: Jun. 8, 2021

(54) ILLUMINATION USING MULTIPLE LIGHT SOURCES

(71) Applicant: Sensor Electronic Technology, Inc., Columbia, SC (US)

(72) Inventors: Maxim S. Shatalov, Columbia, SC (US); Alexander Dobrinsky, Vienna, VA (US)

(73) Assignee: Sensor Electronic Technology, Inc., Columbia, SC (US)

( * ) Notice: Subject to any disclaimer, the term of this patent is extended or adjusted under 35 U.S.C. 154(b) by 123 days.

(21) Appl. No.: 16/369,540

(22) Filed: Mar. 29, 2019

(65) Prior Publication Data

US 2019/0299260 A1    Oct. 3, 2019

Related U.S. Application Data

(60) Provisional application No. 62/651,156, filed on Mar. 31, 2018, provisional application No. 62/651,157, filed on Mar. 31, 2018, provisional application No. 62/651,158, filed on Mar. 31, 2018.

(51) Int. Cl.
| | | |
|---|---|---|
| *B08B 7/00* | (2006.01) | |
| *A61L 2/24* | (2006.01) | |
| *A61L 2/10* | (2006.01) | |

(52) U.S. Cl.
CPC .............. *B08B 7/0057* (2013.01); *A61L 2/10* (2013.01); *A61L 2/24* (2013.01); *A61L 2202/11* (2013.01); *A61L 2202/122* (2013.01); *A61L 2202/14* (2013.01)

(58) Field of Classification Search
CPC .......... A61L 2/24; A61L 2/10; A61L 2202/14; A61L 2202/11; A61L 2202/122
USPC ..................................................... 250/370.11
See application file for complete search history.

(56) References Cited

U.S. PATENT DOCUMENTS

| | | |
|---|---|---|
| 7,553,456 B2 | 6/2009 | Gaska et al. |
| 7,634,996 B2 | 12/2009 | Gaska et al. |
| 8,277,734 B2 | 10/2012 | Koudymov et al. |
| 8,872,131 B2 * | 10/2014 | Rozenberg ............... C02F 1/32 250/455.11 |
| 8,980,178 B2 | 3/2015 | Gaska et al. |
| 9,006,680 B2 | 4/2015 | Bettles et al. |
| 9,034,271 B2 | 5/2015 | Shur et al. |
| 9,061,082 B2 | 6/2015 | Gaska et al. |
| 9,138,499 B2 | 9/2015 | Bettles et al. |
| 9,179,703 B2 | 11/2015 | Shur et al. |
| 9,550,004 B2 | 1/2017 | Smetona et al. |
| 9,572,903 B2 | 2/2017 | Dobrinsky |
| 9,603,960 B2 | 3/2017 | Dobrinsky et al. |
| 9,687,577 B2 | 6/2017 | Dobrinsky et al. |
| 9,707,307 B2 | 7/2017 | Shur et al. |
| 9,718,706 B2 | 8/2017 | Smetona et al. |

(Continued)

*Primary Examiner* — David P Porta
*Assistant Examiner* — Gisselle M Gutierrez
(74) *Attorney, Agent, or Firm* — LaBatt, LLC

(57) ABSTRACT

A solution for illuminating an area and/or treating a substance with light, such as ultraviolet radiation, is described. The solution can use one or more solid state ultraviolet sources in conjunction with one or more ultraviolet lamps to illuminate a treatment region with ultraviolet radiation. A control component can individually operate the solid state ultraviolet source(s) and the ultraviolet lamp(s) to illuminate the treatment region with ultraviolet radiation having a predetermined minimum ultraviolet intensity.

20 Claims, 5 Drawing Sheets

(56) References Cited

U.S. PATENT DOCUMENTS

| | | |
|---|---|---|
| 9,724,441 B2 | 8/2017 | Shur et al. |
| 9,750,830 B2 | 9/2017 | Shur et al. |
| 9,757,486 B2 | 9/2017 | Dobrinsky et al. |
| 9,795,699 B2 | 10/2017 | Shur et al. |
| 9,801,965 B2 | 10/2017 | Betties et al. |
| 9,802,840 B2 | 10/2017 | Shturm et al. |
| 9,855,352 B2 | 1/2018 | Dobrinsky et al. |
| 9,878,061 B2 | 1/2018 | Shur et al. |
| 9,919,068 B2 | 3/2018 | Shur et al. |
| 9,974,877 B2 | 5/2018 | Bettles et al. |
| 9,981,051 B2 | 5/2018 | Shur et al. |
| 9,987,383 B2 | 6/2018 | Bilenko et al. |
| 9,999,782 B2 | 6/2018 | Shur et al. |
| 10,004,821 B2 | 6/2018 | Dobrinsky et al. |
| 10,025,028 B2 | 7/2018 | Dobrinsky et al. |
| 10,040,699 B2 | 8/2018 | Smetona et al. |
| 10,099,944 B2 | 10/2018 | Smetona et al. |
| 10,166,307 B2 | 1/2019 | Dobrinsky et al. |
| 2013/0048545 A1 | 2/2013 | Shatalov et al. |
| 2013/0323120 A1* | 12/2013 | Ma ............... A61L 2/24 422/24 |
| 2014/0096792 A1* | 4/2014 | Brown ........... H01L 21/67028 134/1.3 |
| 2014/0166590 A1* | 6/2014 | Rozenberg .......... C02F 1/008 210/746 |
| 2014/0202962 A1 | 7/2014 | Bilenko et al. |
| 2015/0008167 A1* | 1/2015 | Shturm ............ C02F 1/325 210/85 |
| 2015/0246148 A1* | 9/2015 | Blechschmidt ....... A61L 9/20 422/4 |
| 2015/0265735 A1* | 9/2015 | Ma .................. A61M 39/165 422/24 |
| 2015/0336810 A1* | 11/2015 | Smetona ............ C02F 1/325 210/96.1 |
| 2015/0344329 A1* | 12/2015 | Smetona ............ C02F 1/325 250/437 |
| 2016/0339127 A1* | 11/2016 | Ma .................. A61M 39/165 |
| 2017/0057842 A1 | 3/2017 | Dobrinsky et al. |
| 2017/0100495 A1 | 4/2017 | Shur et al. |
| 2017/0189711 A1 | 7/2017 | Shur et al. |
| 2017/0245527 A1 | 8/2017 | Dobrinsky et al. |
| 2017/0245616 A1 | 8/2017 | Lakios et al. |
| 2017/0281812 A1 | 10/2017 | Dobrinsky et al. |
| 2017/0290934 A1 | 10/2017 | Dobrinsky et al. |
| 2017/0368215 A1 | 12/2017 | Shatalov et al. |
| 2018/0028700 A1 | 2/2018 | Dobrinsky et al. |
| 2018/0071414 A1* | 3/2018 | Dujowich .......... A61L 2/0047 |
| 2018/0092308 A1 | 4/2018 | Dobrinsky et al. |
| 2018/0104368 A1 | 4/2018 | Dobrinsky et al. |
| 2018/0117194 A1 | 5/2018 | Dobrinsky et al. |
| 2018/0185529 A1 | 7/2018 | Shur et al. |
| 2018/0221521 A1 | 8/2018 | Shur et al. |
| 2018/0243458 A1 | 8/2018 | Shatalov et al. |
| 2018/0339075 A1 | 11/2018 | Kennedy et al. |
| 2019/0030196 A1 | 1/2019 | Bilenko et al. |
| 2019/0030477 A1 | 1/2019 | Shatalov |
| 2019/0098842 A1 | 4/2019 | Barber, III et al. |
| 2019/0099613 A1 | 4/2019 | Estes et al. |
| 2019/0100445 A1 | 4/2019 | Dobrinsky |
| 2019/0100718 A1 | 4/2019 | Estes et al. |
| 2019/0117811 A1 | 4/2019 | Barber, III |
| 2019/0125907 A1 | 5/2019 | Dobrinsky |
| 2019/0135659 A1* | 5/2019 | Smetona ............ C02F 1/325 |
| 2019/0201570 A1 | 7/2019 | Dobrinsky et al. |
| 2019/0231912 A1 | 8/2019 | Dobrinsky et al. |
| 2019/0263680 A1 | 8/2019 | Dobrinsky |
| 2019/0300391 A1 | 10/2019 | Shatalov et al. |

* cited by examiner

ILLUMINATION USING MULTIPLE LIGHT SOURCES

REFERENCE TO RELATED APPLICATIONS

The current application claims the benefit of U.S. Provisional Application No. 62/651,156, filed on 31 Mar. 2018, U.S. Provisional Application No. 62/651,157, filed on 31 Mar. 2018, and U.S. Provisional Application No. 62/651,158, filed on 31 Mar. 2018, each of which is hereby incorporated by reference.

TECHNICAL FIELD

The disclosure relates generally to illumination, and more particularly, to illumination with multiple types of light sources, e.g., as part of treating a substance using ultraviolet radiation.

BACKGROUND ART

Treatment of surfaces, fluids, and objects using ultraviolet (UV) radiation offers many advantages over other forms of treatment, such as chemical treatment. For example, treatment with UV radiation does not introduce additional chemical or biological contaminants. Furthermore, ultraviolet radiation provides one of the most efficient approaches to decontamination since there are no microorganisms known to be resistant to ultraviolet radiation, unlike other decontamination methods, such as chlorination. UV radiation is known to be highly effective against bacteria, viruses, algae, molds and yeasts. For example, the hepatitis virus has been shown to survive for considerable periods of time in the presence of chlorine, but is readily eliminated by UV radiation treatment. The removal efficiency of UV radiation for most microbiological contaminants, such as bacteria and viruses, generally exceeds 99%. To this extent, UV radiation is highly efficient at eliminating *E-coli, Salmonella*, Typhoid fever, Cholera, Tuberculosis, Influenza Virus, Polio Virus, and Hepatitis A Virus.

In general, it is desirable that the ultraviolet radiation comprises wavelength(s) that are close to the absorption peak(s) of biologically significant molecules of DNA and/or proteins of a target impurity. Intensity, radiation wavelength, and duration of radiation are important parameters in determining the disinfection rate of UV radiation treatment. These parameters can vary based on a particular target impurity. For example, impurities, such as a bacterium, a virus, a protozoan, a germ, etc., comprise DNA/proteins having corresponding absorption peaks. By exposing the DNA/proteins to ultraviolet radiation having a wavelength close to the absorption peak(s) for a sufficient time and at a sufficient power, the impurity is destroyed. The UV radiation does not allow microorganisms to develop an immune response, unlike the case with chemical treatment. The UV radiation affects biological agents by fusing and damaging the DNA of microorganisms, and preventing their replication. Also, if a sufficient amount of a protein is damaged in a cell of a microorganism, the cell enters apoptosis or programmed death.

Ultraviolet radiation disinfection using mercury based lamps is a well-established technology. Low-pressure and medium-pressure mercury lamps provide a linear spectrum of radiation with some lines, which wavelengths are in the relative vicinity to a DNA absorption line. A low-pressure mercury lamp with a main peak at 253.4 nm often is used in low-consumption residential water and air purification systems. Medium-pressure mercury lamps with a higher radiation power have a multi-peak radiation spectrum and often are used in municipal systems with medium and high water consumption.

More recently, deep ultraviolet (DUV) light emitting device (LED)-based technology has been proposed as an alternative to the use of mercury based lamps in certain disinfection applications. Each technology offers different advantages and disadvantages. For example, in comparison to mercury vapor lamps, DUV LEDs: have substantially longer operating lifetimes (e.g., by a factor of ten); do not include hazardous components (e.g., mercury), which require special disposal and maintenance; are more durable in transit and handling (e.g., no filaments or glass); have a faster startup time; have a lower operational voltage; are less sensitive to power supply intermittency; are more compact and portable; and/or the like. Nonetheless, mercury based lamps remain a suitable option for many disinfection applications.

SUMMARY OF THE INVENTION

Aspects of the invention provide a solution for illuminating an area and/or treating a substance with light, such as ultraviolet radiation. The solution can use one or more solid state ultraviolet sources in conjunction with one or more ultraviolet lamps to illuminate a treatment region with ultraviolet radiation. A control component can individually operate the solid state ultraviolet source(s) and the ultraviolet lamp(s) to illuminate the treatment region with ultraviolet radiation having a predetermined minimum ultraviolet intensity.

A first aspect of the invention provides a system comprising: a set of ultraviolet transparent windows defining at least a portion of at least one side of a treatment region; a set of solid state ultraviolet sources configured to emit ultraviolet light directed through an ultraviolet transparent window of the set of ultraviolet transparent windows into the treatment region; a set of ultraviolet lamps configured to emit ultraviolet light directed through an ultraviolet transparent window of the set of ultraviolet transparent windows into the treatment region; and a control component configured to individually operate the set of solid state ultraviolet sources and the set of ultraviolet lamps to treat a substance located within the treatment region by illuminating the treatment region with ultraviolet radiation having a predetermined minimum ultraviolet intensity.

A second aspect of the invention provides a system comprising: a set of ultraviolet transparent windows defining at least a portion of at least one side of a treatment region; a plurality of solid state ultraviolet sources configured to emit ultraviolet light directed through an ultraviolet transparent window of the set of ultraviolet transparent windows into the treatment region; an ultraviolet lamp configured to emit ultraviolet light directed through an ultraviolet transparent window of the set of ultraviolet transparent windows into the treatment region; and a control component configured to individually operate the plurality of solid state ultraviolet sources and the ultraviolet lamp to treat a substance located within the treatment region by illuminating the treatment region with ultraviolet radiation having a predetermined minimum ultraviolet intensity, wherein the control component illuminates the treatment region by concurrently turning on at least some of the plurality of solid state ultraviolet sources and the ultraviolet lamp and reducing power to the at least some of the plurality of solid state ultraviolet sources over time in response to the ultraviolet lamp emitting a higher intensity of ultraviolet radiation.

A third aspect of the invention provides a lighting system comprising: a set of transparent windows defining at least a portion of at least one side of an illumination region; a plurality of solid state light sources configured to emit light directed through a transparent window of the set of transparent windows into the illumination region; a lamp configured to emit light directed through a transparent window of the set of transparent windows into the illumination region; and a control component configured to individually operate the plurality of solid state light sources and the lamp to illuminate the illumination region with light having a predetermined minimum light intensity.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
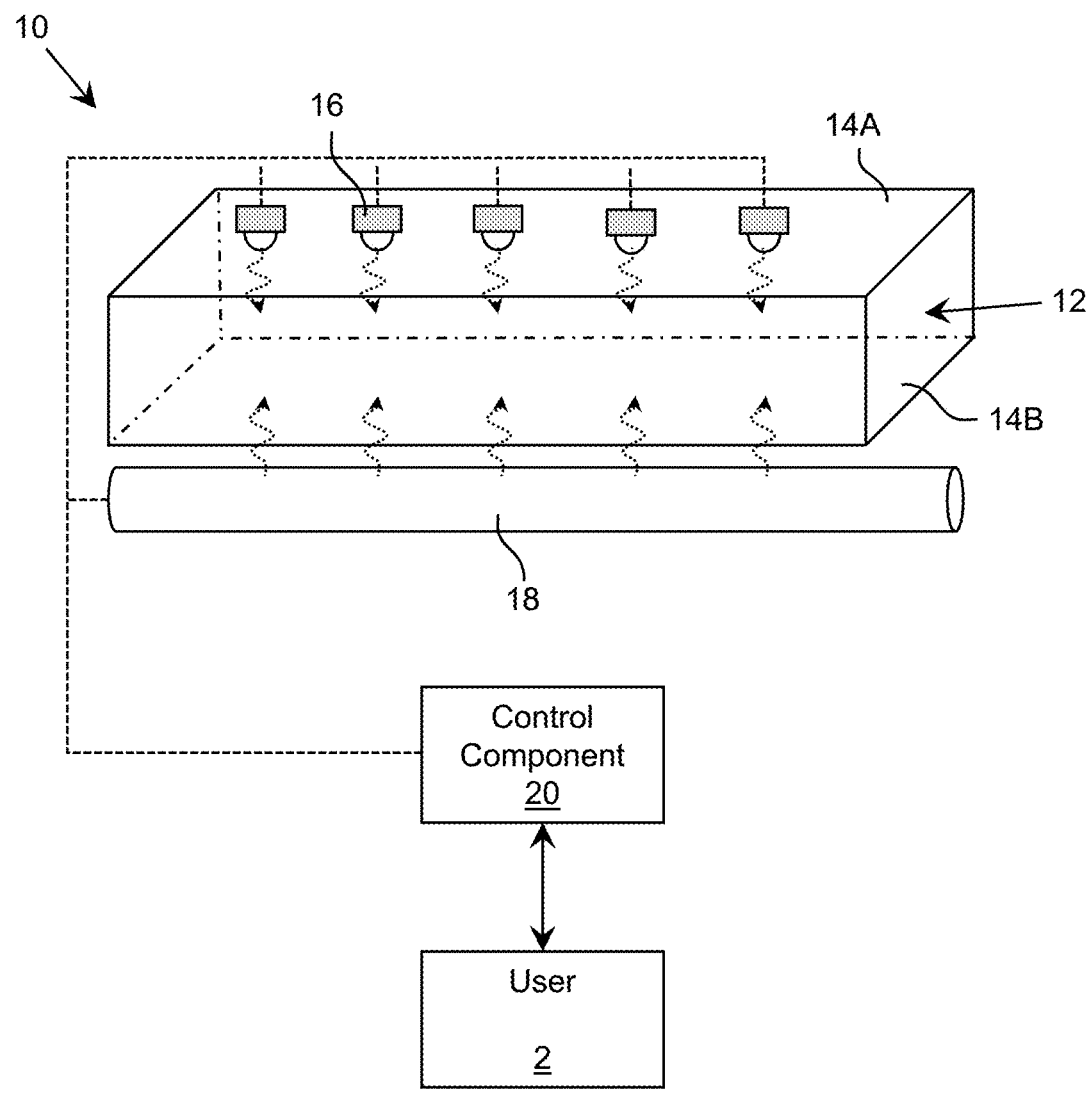
FIG. 1 shows a schematic view of an illustrative treatment system according to an embodiment.

As indicated above, aspects of the invention provide a solution for illuminating an area and/or treating a substance with light, such as ultraviolet radiation. The solution can use one or more solid state ultraviolet sources in conjunction with one or more ultraviolet lamps to illuminate a treatment region with ultraviolet radiation. A control component can individually operate the solid state ultraviolet source(s) and the ultraviolet lamp(s) to illuminate the treatment region with ultraviolet radiation having a predetermined minimum ultraviolet intensity.

It is understood that, unless otherwise specified, each value is approximate and each range of values included herein is inclusive of the end values defining the range. As used herein, unless otherwise noted, the term "approximately" is inclusive of values within +/−ten percent of the stated value, while the term "substantially" is inclusive of values within +/−five percent of the stated value. Unless otherwise stated, two values are "similar" when the smaller value is within +/−twenty-five percent of the larger value.

As also used herein, a material/structure/layer is considered to be "transparent" when the material/structure/layer allows at least ten percent of radiation having a target wavelength, which is radiated at a normal incidence to an interface of the material/structure/layer, to pass there through. Furthermore, as used herein, a material/structure/layer is considered to be "reflective" when the material/structure/layer reflects at least thirty percent of radiation having a target wavelength, which is radiated at a normal incidence to an interface of the material/structure/layer. In an embodiment, the target wavelength of the radiation corresponds to a wavelength of radiation emitted or sensed (e.g., peak wavelength+/−five nanometers) by an active region of a corresponding optoelectronic device during operation of the optoelectronic device. For a given material/structure/layer, the wavelength can be measured in a material of consideration and can depend on a refractive index of the material.

As used herein, the terms "sterilization," "purification," "decontamination," "disinfection," and their related terms mean treating a substance, such as an object or a surface thereof, a fluid (e.g., liquid, gas), and/or the like, so that the substance includes a sufficiently low number of contaminants (e.g., chemical, sediment, and/or the like) and microorganisms (e.g., virus, bacteria, and/or the like) so that the substance is safe for the desired interaction with a human or other animal. For example, the treatment (e.g., sterilization, purification, decontamination, or disinfection) of water means that the resulting water has a sufficiently low level of microorganisms and other contaminants so that a typical human or other animal can interact with (e.g., consume or otherwise use) the water without suffering adverse effects from microorganisms and/or contaminants present in the water. A target level of microorganisms and/or contaminants for a particular substance and/or an intended interaction with the substance can be defined, for example, by a standards setting organization, such as a governmental organization.

Ultraviolet radiation, which can be used interchangeably with ultraviolet light, means electromagnetic radiation having a wavelength ranging from approximately 10 nm to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm. It is understood that a light emitting source configured to operate in a particular range can emit ultraviolet radiation in an adjacent range. For example, as used herein, a UV-C source can also emit UV-B radiation, e.g., 280 nm to 290 nm. As used herein, blue-UV radiation includes at least a portion of the UV-A electromagnetic radiation as well as higher wavelength visible light, e.g., visible light having a wavelength ranging from approximately 400 nm to approximately 460 nm (360 nm to 460 nm in a more particular embodiment).

Generally, ultraviolet radiation, and in particular, UV-B radiation and UV-C radiation is "germicidal," i.e., it deactivates the DNA of bacteria, viruses and other pathogens, and thus, destroys their ability to multiply and cause disease. This effectively results in sterilization of the microorganisms. Specifically, UV-B radiation and UV-C radiation cause damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies.

Ultraviolet radiation with a wavelength of approximately between about 250 nm to about 290 nm provides the highest germicidal effectiveness, while an ultraviolet radiation between about 260 nm to about 310 nm is sufficient for providing overall germicidal effectiveness, and ultraviolet radiation between 260 nm to 270 nm is a preferred range for facilitating disinfection, sterilization of fluids. While susceptibility to ultraviolet radiation varies, exposure to ultraviolet energy in the above range for about 20 to about 34 milliwatt-seconds/cm$^2$ is adequate to deactivate approximately 99 percent of the pathogens.

Turning to the drawings, FIG. 1 shows a schematic view of an illustrative treatment system 10 according to an embodiment. The treatment system 10 includes a treatment region 12 within which a substance can be located for treatment. The treatment region 12 can comprise any type of region, depending on the substance being treated. For example, the treatment region 12 can comprise a passageway (or a section thereof) along which the substance is moving. In a more particular embodiment, the passageway can comprise a conduit (e.g., a channel) through which a fluid is flowing. In another embodiment, the treatment region 12 can comprise a conveyor (or a section thereof) used to transport one or more of various types of objects. In still another embodiment, the treatment region 12 can comprise a container within which substance(s) to be treated are placed.

Regardless, the treatment region 12 can be at least partially defined by a set of ultraviolet transparent windows 14A, 14B. Each ultraviolet transparent window 14A, 14B can be formed of any suitable ultraviolet transparent material. Illustrative ultraviolet transparent materials comprise silicon dioxide ($SiO_2$), aluminum oxide ($Al_2O_3$), a fluoropolymer, $SiO_2$ derivatives such as moldable silicone, calcium fluoride ($CaF_2$), magnesium fluoride ($MgF_2$), and/or the like. Ultraviolet transparent fluoropolymers that can be used for an ultraviolet transparent window 14A, 14B can include a terpolymer of ethyelene, tetrafluoroethylene, and hexafluoropropylene (EFEP), an amorphous fluoropolymer (e.g., Cytop®), polytetrafluoroethylene (e.g., Teflon®), and/or the like. An ultraviolet transparent window 14A, 14B can define substantially all of a side of the treatment region 12 or only a portion of a side of the treatment region. In an embodiment, one or more other sides of the treatment region 12 comprise an ultraviolet reflective material, which can enable recirculation of ultraviolet radiation within the treatment region 12.

In an embodiment, one or more internal surfaces defining the treatment region 12 can comprise a photocatalyst material. For example, the photocatalyst material can include an ultraviolet active photocatalyst located on an inner wall surface of each of the receptacles. The ultraviolet active photocatalyst is configured to undergo a photocatalytic reaction in response to being irradiated by ultraviolet light, such as UV-A, blue-UV, and/or UV-B light. The photocatalytic reaction facilitates removal and suppression of any harmful contaminants present on the corresponding surface and/or a substance located with the treatment region 12. In one embodiment, the photocatalytic reaction can include forming reactive oxygen species (ROS) that interact and disrupt the proliferation of the harmful contaminants.

The treatment system 10 is shown including two types of ultraviolet sources. In particular, the treatment system 10 is shown including a set of solid state ultraviolet sources 16. A solid state ultraviolet source 16 can comprise any type of semiconductor emitting device, which can be operated to emit ultraviolet radiation. An illustrative solid state ultraviolet source 16 includes a conventional or super luminescent ultraviolet light emitting diode (LED), a deep ultraviolet LED, an ultraviolet light emitting solid state laser, an ultraviolet laser diode of any of various types, and/or the like. As used herein, a solid state ultraviolet source emits electromagnetic radiation having a peak wavelength within the ultraviolet radiation or deep ultraviolet radiation range of wavelengths. Additionally, a solid state ultraviolet source can emit electromagnetic radiation having a peak wavelength outside of the ultraviolet radiation range of wavelengths, but a full width at half maximum (FWHM) which partially extends into the ultraviolet radiation range of wavelengths.

The solid state ultraviolet sources 16 can be configured to emit a plurality of distinct ultraviolet wavelengths. For example, the solid state ultraviolet sources 16 can include multiple subsets of solid state ultraviolet sources 16, each of which is configured to emit ultraviolet light having a different range of ultraviolet wavelengths. Each range of ultraviolet wavelengths can be at least partially located in any of: UV-A, UV-B, or UV-C. To this extent, two subsets of solid state ultraviolet sources 16 can emit UV-C radiation of different peak wavelengths. In an embodiment, the solid state ultraviolet sources 16 include at least a first subset which emit UV-A or blue-UV light, and at least a second subset which emit UV-C ultraviolet light.

Additionally, the treatment system 10 is shown including an ultraviolet lamp 18. The ultraviolet lamp 18 can comprise any type of lamp that emits ultraviolet radiation. An illustrative ultraviolet lamp 18 comprises a mercury-based ultraviolet lamp, such as a mercury vapor lamp. Other illustrative ultraviolet lamps 18 include ultraviolet fluorescent lamps, ultraviolet incandescent lamps, other ultraviolet gas-discharge lamps, and/or the like. Additionally, it is understood that a treatment system described herein can include other types of light sources, such as a visible light source, an infrared light source, and/or the like. Such light sources can comprise lamps and/or solid state light sources.

During operation of an ultraviolet source 16, 18, a corresponding ultraviolet transparent window 14A, 14B can allow ultraviolet light emitted by the ultraviolet source 16, 18 to pass there through and into the treatment region 12. Additionally, the ultraviolet transparent window 14A, 14B can prevent interaction between the substance being treated with ultraviolet radiation within the treatment region 12 and other components of the system, such as the ultraviolet sources 16, 18 emitting the ultraviolet radiation. In an embodiment, various components of the system, including the ultraviolet sources 16, 18, are hermetically isolated from the ambient within the treatment region 12.

Figure 2A:
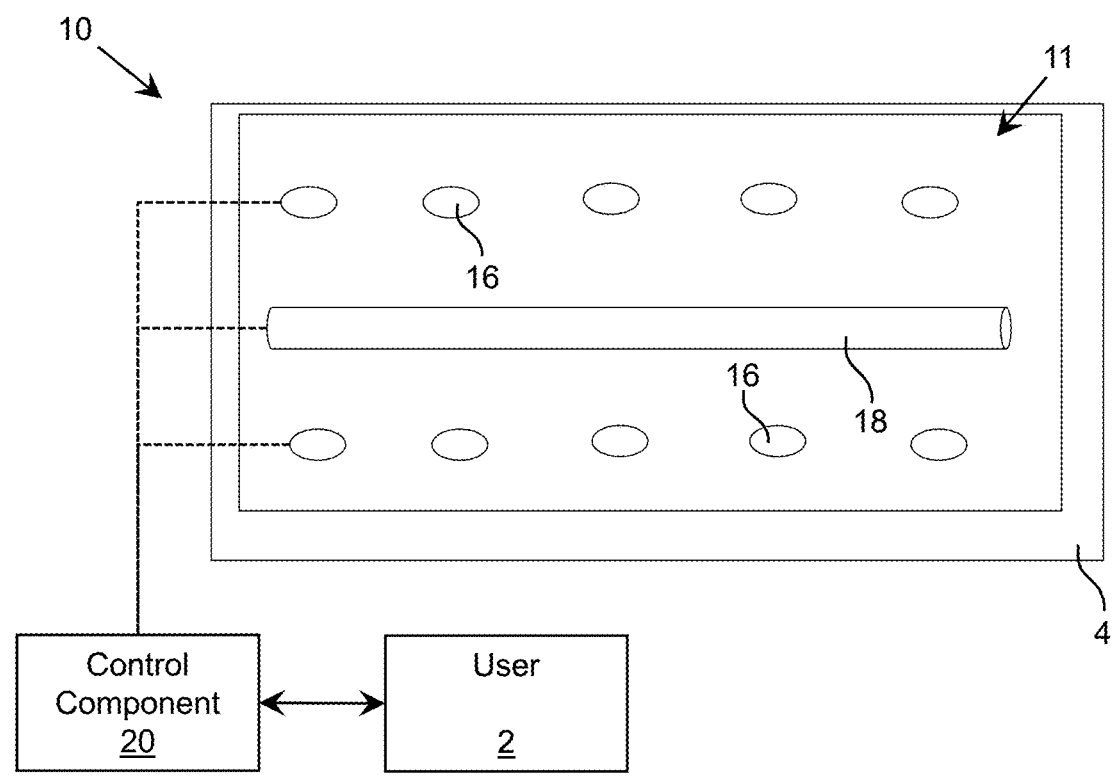
FIGS. 2A and 2B show schematic views of an illustrative treatment system according to another embodiment.
Figure 2B:
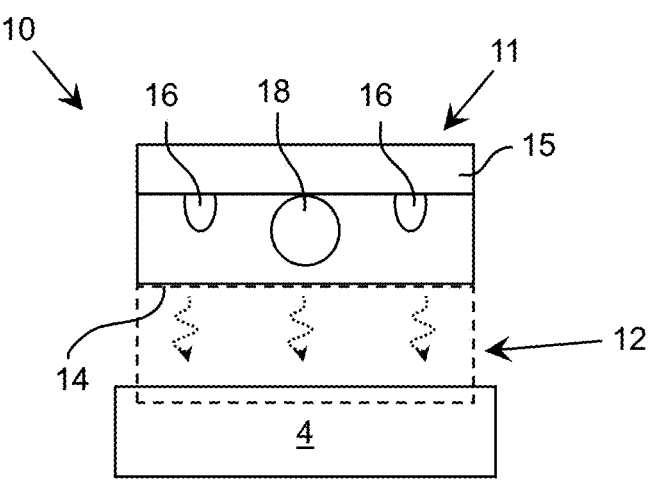

FIGS. 2A and 2B show schematic views of an illustrative treatment system 10 according to another embodiment. In this case, both types of ultraviolet sources 16, 18 are located on the same side of a treatment region 12 (shown in FIG. 2B) in a single illuminating unit 11. The illuminating unit 11 can include a substrate 15, on which the ultraviolet sources 16, 18 are mounted. The substrate 15 can comprise any type of substrate, such as a printed circuit board. To this extent, the substrate 15 can include additional components and/or electrical wiring, which enables a control component 20 to operate the ultraviolet sources 16, 18 in order to treat a substance 4 as described herein.

The illuminating unit 11 and/or the substance 4 can be moved with respect to each other. For example, the illuminating unit 11 can comprise a relocatable unit, such as a handheld unit or a machine mounted unit, which can be moved with respect to a surface of the substance 4 requiring treatment. Additionally, the substance 4 can move with respect to a location of the illuminating unit 11, such as along a conveyor, or the like. In either case, a surface of the substance 4 can be located within a treatment region 12 for illumination by the ultraviolet sources 16, 18. The treatment region 12 can be defined as an area within which the ultraviolet radiation has a predetermined minimum ultraviolet intensity in order to effectively treat any substance located therein.

Referring to FIGS. 1-2B, the treatment system 10 can include a control component 20, which is operatively connected to the ultraviolet sources 16, 18. For example, an output of the control component 20 can be configured to selectively apply power to each of the ultraviolet sources 16, 18. Alternatively, the control component 20 can communicate with (e.g., using any wired and/or wireless communications solution) and direct operation of an intermediary device, which controls the power applied to the ultraviolet sources 16, 18. Regardless, the control component 20 can individually operate the ultraviolet sources 16, 18 to treat a substance located within the treatment region 12. To this extent, the control component 20 can operate the ultraviolet sources 16, 18 to illuminate the treatment region 12, and a substance located therein, with ultraviolet radiation. The treatment can be performed through control of a user 2 and/or automatically by the control component 20, e.g., after a triggering event, analysis of the substance, and/or the like.

The control component 20 can be configured to operate each ultraviolet source 16, 18 independently. In an embodiment, the control component 20 can be configured to operate two or more ultraviolet sources as a group. For example, the solid state ultraviolet sources 16 may include different subsets, each of which emits ultraviolet radiation of a different wavelength (e.g., UV-A, UV-C). In this case, depending on the treatment being performed and/or one or more attributes of the substance and/or a target contaminant, the control component 20 can operate a corresponding subset of the solid state ultraviolet sources 16. For example, different contaminants may have different wavelengths of ultraviolet radiation that provide an optimal disinfection rate. In this case, depending on the target contaminant, the control component 20 can operate a corresponding subset of the solid state ultraviolet sources 16 to emit ultraviolet radiation having the wavelength that provides the optimal disinfection rate.

Embodiments of a treatment system described herein can be configured to prevent overheating of the solid state ultraviolet sources 16 during their operation. For example, the control component 20 can activate the solid state ultraviolet sources 16 in a pulsed mode of operation to prevent the solid state ultraviolet sources 16 from overheating. To this extent, the treatment system can operate the solid state ultraviolet sources 16 in two or more subsets, which are turned on and off in a sequence designed to provide a uniform ultraviolet radiation intensity, while preventing the solid state ultraviolet sources 16 from overheating. Additionally, a treatment system described herein can include one or more components for extracting heat from the solid state ultraviolet sources 16. For example, one or more heat sinks can be attached to the solid state ultraviolet sources 16 to dissipate heat during the operation thereof. In an embodiment, the solid state ultraviolet sources 16 can be cooled by a flowing fluid next to a heat extraction module. In an embodiment, a treatment component can include a special cooling channel to dissipate heat from the solid state ultraviolet sources 16.

In a treatment system 10 described herein (e.g., the treatment systems of FIG. 1 and FIGS. 2A and 2B), the control component 20 can operate the ultraviolet sources 16, 18 to ensure that the ultraviolet radiation within the treatment region 12 has a predetermined minimum ultraviolet intensity. The predetermined minimum ultraviolet intensity can correspond to a fixed intensity that can be used by default regardless of the conditions within the treatment region 12. In an embodiment, the predetermined minimum ultraviolet intensity can be selected/adjusted by a user 2. Furthermore, the control component 20 can determine/adjust the predetermined minimum ultraviolet intensity based on one or more attributes of the treatment region 12 and/or the substance being treated therein.

For example, in an embodiment, the substance is moving (e.g., falling, flowing, being conveyed, and/or the like) through the treatment region 12. A speed with which the substance is moving will affect a duration with which the substance will be illuminated with the ultraviolet light within the treatment region 12. As a result, to obtain a required dose, an intensity of the ultraviolet radiation can be adjusted based on the speed with which the substance is moving.

To this extent, a treatment system described herein can include one or more substance sensors for acquiring data corresponding to one or more attributes of the substance. For example, the treatment system 10 can include a sensor that acquires data corresponding to a speed/flow rate at which a substance is moving through the treatment region 12. In this case, the control component 20 can determine the predetermined minimum ultraviolet intensity to ensure that the substance receives a minimum dose of ultraviolet radiation while it is present within the treatment region 12. Subsequently, the control component 20 can operate the ultraviolet sources 16, 18 to emit ultraviolet radiation in the treatment region 12 having at least the predetermined minimum ultraviolet intensity.

An embodiment of the treatment system 10 can include a substance sensor for acquiring data corresponding to a transparency of the substance, e.g., when the substance comprises a liquid. The transparency of the substance can affect an intensity of the radiation within an area of the treatment region 12. To this extent, the control component 20 can use the transparency data to adjust an intensity of the ultraviolet sources 16, 18 to ensure that the predetermined minimum ultraviolet intensity is present within all of the treatment region 12.

The treatment system 10 also can include one or more substance sensors for acquiring data corresponding to a level of contamination of the substance. For example, the treatment system 10 can include one or more emitters that generate radiation that induces a contaminant to fluoresce, which can be detected by one or more sensors. Similarly, the treatment system 10 can include one or more substance sensors, with or without corresponding emitters, to acquire data regarding a visible appearance of a substance, a chemical composition, and/or the like. The control component 20 can operate the emitter(s) and/or the substance sensor(s) and determine a level of contamination based on the data acquired by the sensors. The control component 20 can determine the predetermined minimum ultraviolet intensity using the level of contamination. For example, when no or a very low level of contamination is detected, the control component 20 can use a low predetermined minimum ultraviolet intensity to deliver a low dose of ultraviolet radiation to suppress any potential growth. In contrast, when a high level of contamination is detected, the control component 20 can use a high predetermined minimum ultraviolet intensity to quickly reduce the level of contamination.

In an embodiment, the treatment system 10 can include one or more substance sensors configured to provide feedback data to the control component 20. For example, the feedback data can comprise fluorescence data, visible data, chemical data, and/or the like, for the substance after being treated within the treatment region. The control component 20 can determine an effectiveness of the treatment using the feedback data and adjust operation accordingly. For example, the control component 20 can determine changes in the fluorescent and/or visible appearance and/or chemical composition of the substance using similar data acquired for the substance prior to the treatment. Subsequently, the control component 20 can perform additional treatment on the substance, adjust one or more parameters used for subsequent treatment of a similar substance, and/or the like. The feedback sensor(s) can be located after a substance passes through the treatment region 12 and/or be located within the treatment region 12, e.g., when the substance is not moving relative to the treatment region 12.

Additionally, a treatment system described herein can include one or more environment sensors, which are configured to acquire data regarding the treatment region 12. For example, a treatment system can include one or more ultraviolet sensors located within the treatment region 12, which can provide data regarding an overall intensity of the ultraviolet radiation therein, e.g., due to a combination of the ultraviolet sources 16, 18. Such data can be used by the control component 20 to adjust operation of one or more of the ultraviolet sources 16, 18 (e.g., to attain a predetermined minimum ultraviolet intensity at one or more locations within the treatment region), provide feedback to a user 2 (e.g., to move an illuminating unit 11 closer to or further from a surface), determine a transparency of the substance, and/or the like.

Embodiments of a treatment system described herein can include one or more features configured to provide a uniform distribution of intensity of ultraviolet radiation over the treatment region 12. As used herein, a distribution of intensity is considered to be uniform when a ratio between the maximum intensity and a minimum intensity for a given area is at most twice. For example, an ultraviolet transparent window described herein can comprise an exit surface of a light guiding layer, which is includes one or more features to diffusively transmit ultraviolet light emitted from the ultraviolet sources 16, 18.

Figure 3A:
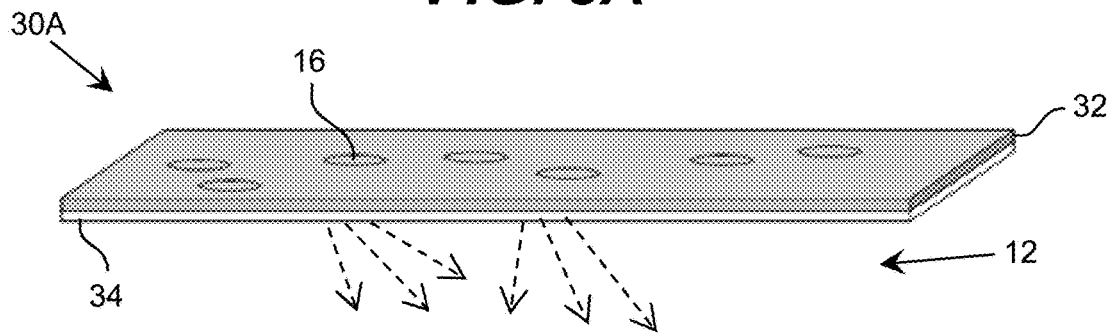
FIGS. 3A-3C show illustrative light guiding structures according to embodiments.
Figure 3B:
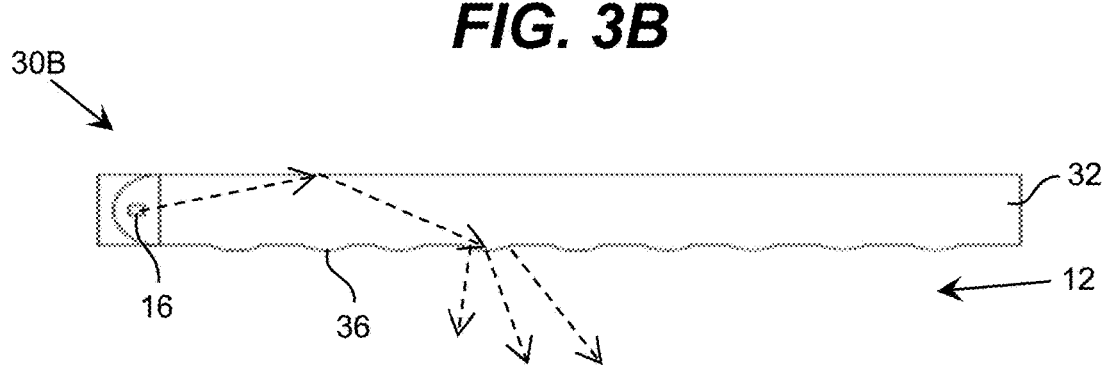
Figure 3C:
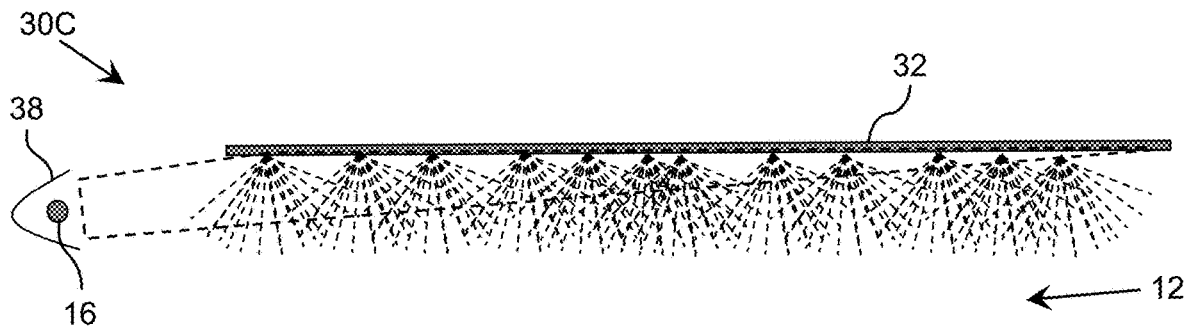

FIGS. 3A-3C show illustrative light guiding layers according to embodiments. While these light guiding layers are illustrated in conjunction with illustrative arrangements of solid state ultraviolet sources, it is understood that the light guiding layers can be configured for use with various arrangements of various ultraviolet sources, including one or more ultraviolet lamps. It is understood that the light guiding layers shown and described herein are only illustrative of various possible configurations. To this extent, it is understood that a light guiding layer can comprise any of various types of ultraviolet transparent wave guiding material including, but not limited to, an ultraviolet fiber, a diffusive ultraviolet emitter, scattering elements, an ultraviolet transparent fluid, and/or the like. Furthermore, a light guiding structure can comprise multiple light guiding layers. For example, other light guiding structures are shown and described in: U.S. Pat. No. 9,550,004, issued 24 Jan. 2017; U.S. Pat. No. 9,855,352, issued on 2 Jan. 2018; U.S. Pat. No. 10,025,028, issued 17 Jul. 2018; and U.S. patent application Ser. No. 16/142,927, filed on 26 Sep. 2018, each of which is hereby incorporated by reference.

FIG. 3A shows a schematic of a light guiding structure 30A operating in conjunction with a set of solid state ultraviolet sources 16 to irradiate a treatment region 12 according to an embodiment. As illustrated, the light guiding structure 30A includes a light guiding layer 32, which can be optically coupled to the set of solid state ultraviolet sources 16. As used herein, a light guiding layer means a transparent material that is configured to guide ultraviolet light therein for transmission at one or more predetermined locations. To this extent, the ultraviolet light emitted from the solid state ultraviolet sources 16 can propagate through a region within the light guiding layer 32 before exiting into the treatment region 12. This configuration enables the treatment region 12 to be uniformly irradiated with ultraviolet light emitted from the solid state ultraviolet sources 16. In an embodiment, the light guiding structure 30A can further include an ultraviolet transparent window 34, which can be configured to transmit and/or diffusively the ultraviolet light emitted from the solid state ultraviolet sources 16 and transmitted from the light guiding layer 32 to the treatment region 12.

FIG. 3B shows a schematic of an alternative light guiding structure 30B and solid state ultraviolet source 16 configuration according to an embodiment. As illustrated, the light guiding structure 30B includes a light guiding layer 32 having a set of roughness domains 36 on an exit side of the light guiding layer 32, which direct the ultraviolet light emitted by the solid state ultraviolet source 16 into the treatment region 12. In one embodiment, the exit side of the light guiding layer 32 including the roughness domains 36 can have a diffusive covering material, e.g., in the form of a film or a layer that is configured to diffuse ultraviolet light generated from the solid state ultraviolet source 16. In one embodiment, the diffusive covering material can include, but is not limited to, a fluoropolymer.

As illustrated, the solid state ultraviolet source 16 can be positioned adjacent to a side of the light guiding layer 32 and be configured to emit ultraviolet radiation that is directed at an interior side of the light guiding layer 32. As a result, the ultraviolet light will first reflect off of the interior side of the light guiding layer 32 before being directed out of the light guiding layer 32 and into the treatment region 12. In one embodiment, the solid state ultraviolet source 16 can be adhered to the side of the light guiding layer 32 by an ultraviolet transparent adhesive material, such as a fluoropolymer.

FIG. 3C shows a schematic of another alternative light guiding structure 30C and solid state ultraviolet source 16 configuration according to an embodiment. As illustrated, the light guiding structure 30C can include a parabolic reflector 38 located adjacent to the solid state ultraviolet source 16. The parabolic reflector 38 directs the ultraviolet radiation emitted by the solid state ultraviolet source 16 towards a light guiding layer 32 that can diffusively reflect the ultraviolet radiation towards the treatment region 12. The parabolic reflector 38 can be formed of an ultraviolet reflective material, such as aluminum, a fluoropolymer, and/or the like. The light guiding layer 32 can be formed a material, such as silicon dioxide ($SiO_2$), aluminum oxide ($Al_2O_3$), fluoropolymer, calcium fluoride ($CaF_2$), magnesium fluoride ($MgF_2$), and/or the like.

Returning to FIGS. 1 and 2A-2B, each ultraviolet transparent window shown and described therein can be fabricated from one or more of the light guiding structures. In an embodiment, a treatment system can include multiple disjoint ultraviolet transparent windows, each of which is formed from one or more of the light guiding structures described herein.

Figure 4A:
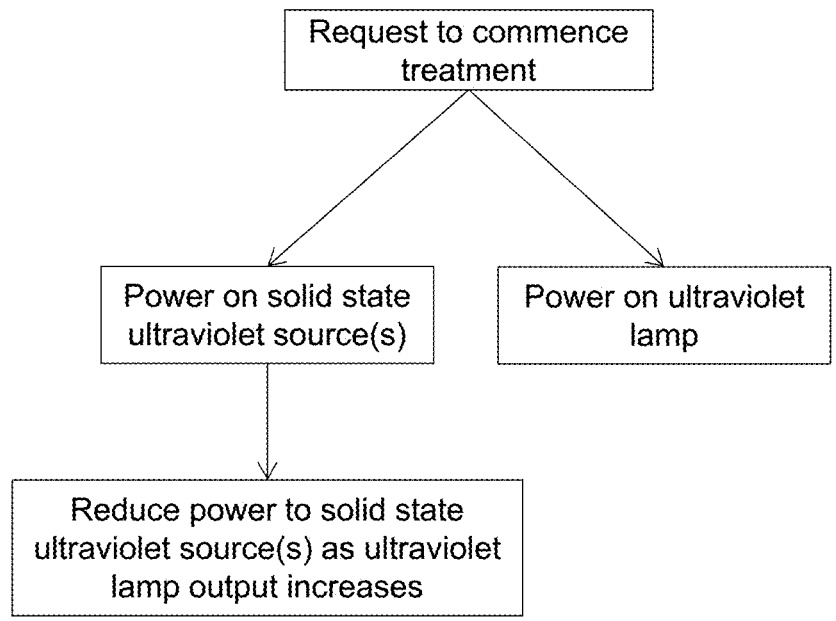
FIGS. 4A and 4B show an illustrative process and power output in response to commencing a treatment according to an embodiment.
Figure 4B:
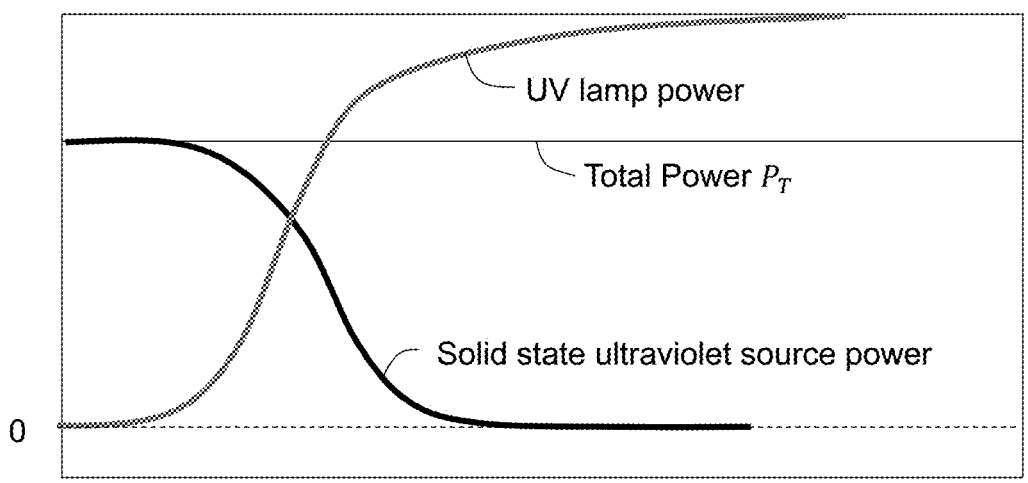

As is known in the art, when an ultraviolet lamp 18 is first powered on, the intensity of the emitted ultraviolet radiation increases ramps up over a period of time. In an embodiment, the control component 20 is configured to operate the ultraviolet sources 16, 18 to provide a minimum ultraviolet intensity within the treatment region 12 while the ultraviolet intensity of the ultraviolet lamp 18 is increasing. FIGS. 4A and 4B show an illustrative process and power output in response to commencing a treatment, which can be implemented by a control component 20 described herein, according to an embodiment. For example, as illustrated in FIG. 4A, in response to a request to commence treatment, the control component 20 can turn on both ultraviolet sources 16, 18. The control component 20 can activate a sufficient number of solid state ultraviolet sources 16 at high power to provide the minimum ultraviolet intensity. As these devices output their maximum upon activation, the resulting minimum ultraviolet intensity will be quickly obtained within the treatment region 12.

After commencing the treatment, the control component 20 can reduce the power provided to the solid state ultraviolet sources 16 as a function of time due to the ultraviolet lamp 18 warming up and the resulting increase in luminous output of the ultraviolet lamp 18. For example, the control component 20 can operate the solid state ultraviolet sources 16 in a pulse mode, which results in a reduced luminous output as well as prevents overheating of the solid state ultraviolet sources 16. In an embodiment, the control component 20 can use a predetermined reduction rate for powering the solid state ultraviolet sources 16 after first powering the ultraviolet lamp 18. Such a reduction rate can depend on the type of ultraviolet lamp 18 being used. For example, some UV-C lamps 18 acquire about 40% of their intensity over a first short period of time, and the control component 20 can reduce the power provided to the solid state ultraviolet sources 16 by a similar amount of power over a similar amount of time.

In another embodiment, the control component 20 can use feedback, e.g., as acquired by an ultraviolet environment sensor, to dynamically determine and adjust the power provided to the solid state ultraviolet sources 16. In an embodiment, after concurrent activation, the power applied to the solid state ultraviolet sources 16 is reduced when the ultraviolet lamp 18 power is at least fifty percent of its maximum power. In another embodiment, the power applied to the solid state ultraviolet sources 16 starts to be reduced at a time T1, when changes to the ultraviolet lamp 18 power over time, dP/dt (at t=T1) is less than half (an order of magnitude in a more particular embodiment) the total power at time T1 (e.g., P(t=T1)(T1)).

Figure 5:
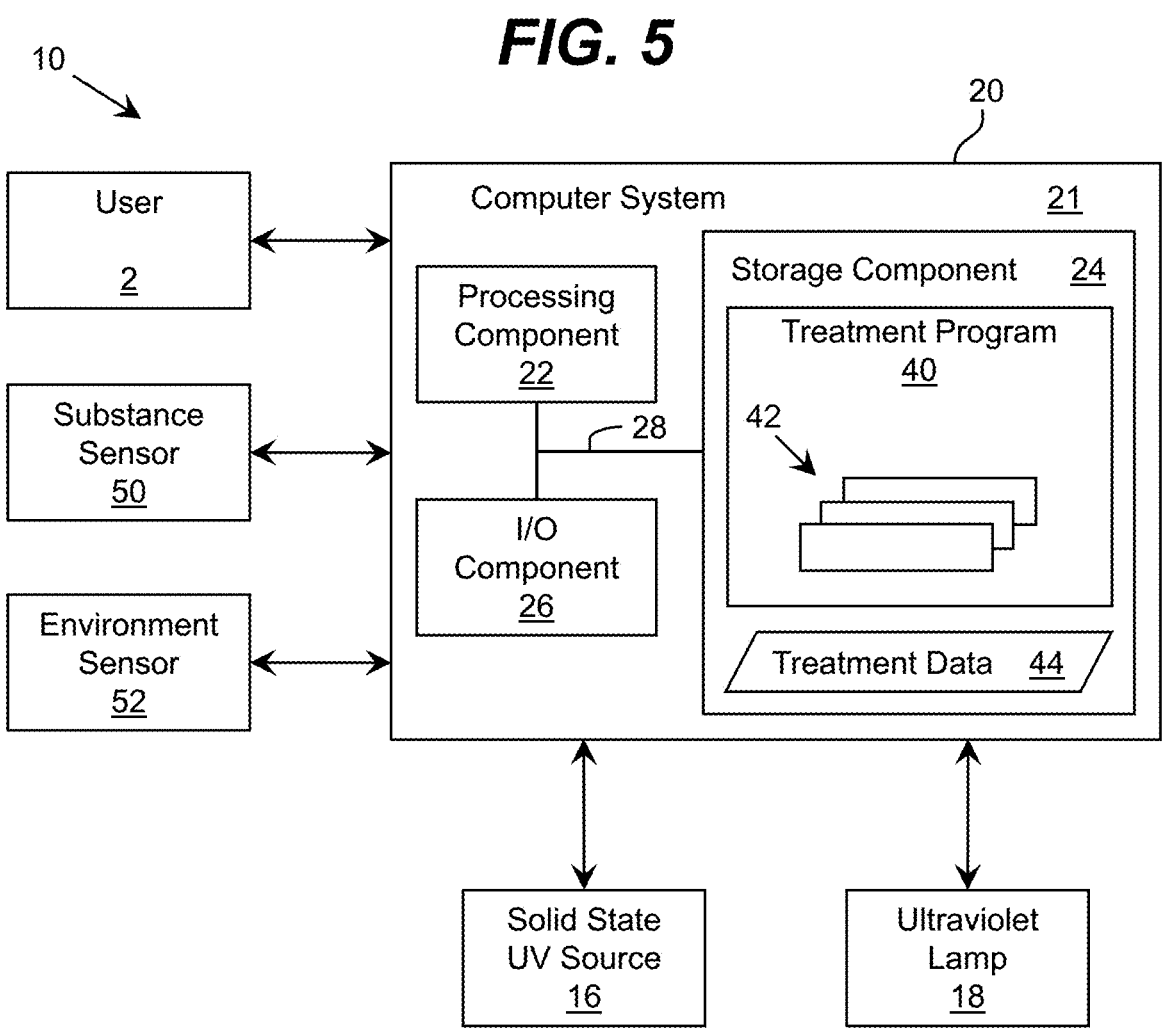
FIG. 5 shows a schematic view of another illustrative treatment system according to an embodiment.

FIG. 5 shows a schematic view of another illustrative treatment system 10 according to an embodiment. To this extent, the treatment system 10 includes a control component 20, which is shown implemented as a computer system 21 that can perform a process described herein in order to treat a substance. In particular, the computer system 21 is shown including a treatment program 40, which makes the computer system 21 operable to treat a substance by performing a process described herein.

The computer system 21 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, the processing component 22 executes program code, such as the treatment program 40, which is at least partially fixed in storage component 24. While executing program code, the processing component 22 can process data, such as the treatment data 44, which can result in reading and/or writing transformed data from/to the storage component 24 and/or the I/O component 26 for further processing. The pathway 28 provides a communications link between each of the components in the computer system 21. The I/O component 26 can comprise one or more human I/O devices, which enable a human user 2 to interact with the computer system 21 and/or one or more communications devices to enable a system user 2 to communicate with the computer system 21 using any type of communications link. To this extent, the treatment program 40 can manage a set of interfaces (e.g., graphical user interface(s), application program interface, and/or the like) that enable human and/or system users 2 to interact with the treatment program 40 and the treatment data 44. Furthermore, the treatment program 40 can manage (e.g., store, retrieve, create, manipulate, organize, present, etc.) the data, such as treatment data 44, using any solution.

In any event, the computer system 21 can comprise one or more general purpose computing articles of manufacture (e.g., computing devices) capable of executing program code, such as the treatment program 40, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the treatment program 40 can be embodied as any combination of system software and/or application software.

Furthermore, the treatment program 40 can be implemented using a set of modules 42. In this case, a module 42 can enable the computer system 21 to perform a set of tasks used by the treatment program 40, and can be separately developed and/or implemented apart from other portions of the treatment program 40. As used herein, the term "component" means any configuration of hardware, with or without software, which implements the functionality described in conjunction therewith using any solution, while the term "module" means program code that enables a computer system 21 to implement the actions described in conjunction therewith using any solution. When fixed in a storage component 24 of a computer system 21 that includes a processing component 22, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 21.

When the computer system 21 comprises multiple computing devices, each computing device can have only a portion of the treatment program 40 fixed thereon (e.g., one or more modules 42). However, it is understood that the computer system 21 and the treatment program 40 are only representative of various possible equivalent computer systems that may perform a process described herein. To this extent, in other embodiments, the functionality provided by the computer system 21 and the treatment program 40 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 21 includes multiple computing devices, the computing devices can communicate over any type of communications link. Furthermore, while performing a process described herein, the computer system 21 can communicate with one or more other computer systems using any type of communications link. In either case, the communications link can comprise any combination of various types of optical fiber, wired, and/or wireless links; comprise any combination of one or more types of networks; and/or utilize any combination of various types of transmission techniques and protocols.

As discussed herein, the control component 20 can treat a substance using ultraviolet radiation. To this extent, the control component 20 can individually operate one or more solid state ultraviolet sources 16 and/or one or more ultraviolet lamps 18 in order to illuminate the substance with ultraviolet radiation having a predetermined minimum ultraviolet intensity. Additionally, the control component 20 can determine the minimum ultraviolet intensity and/or a type of treatment to perform using data acquired by one or more substance sensors 50 (e.g., visible data, fluorescence data, speed/flow rate, transparency, contamination data, and/or the like). Furthermore, the control component 20 can make one or more adjustments to operation of the solid state ultraviolet sources 16 and/or ultraviolet lamps 18 using feedback data acquired by one or more substance sensors 50 and/or data acquired by one or more environment sensors 52 (e.g., measured ultraviolet intensity).

While aspects of the invention have been shown and described in conjunction with illuminating an area and/or treating a substance with ultraviolet radiation having a predetermined minimum ultraviolet intensity, it is understood that embodiments also can ensure that the substance is treated with ultraviolet radiation below a predetermined maximum ultraviolet intensity. To this extent, the control component 20 can manage operation of the solid state ultraviolet sources 16 and/or ultraviolet lamps 18 in a manner that ensures that the ultraviolet radiation remains within a desired range of ultraviolet intensities. In an embodiment, the maximum ultraviolet intensity is four times the minimum ultraviolet intensity. In a more particular embodiment, the maximum ultraviolet intensity is two and a half times the minimum ultraviolet intensity. In this manner, the control component 20 can reduce a possible harmful effect that the ultraviolet radiation may have on the substance.

While shown and described herein as a method and system for illuminating an area and/or treating a substance using ultraviolet radiation, it is understood that aspects of the invention further provide various alternative embodiments. For example, in one embodiment, the invention provides a computer program fixed in at least one computer-readable medium, which when executed, enables a computer system to treat a substance using ultraviolet radiation. To this extent, the computer-readable medium includes program code, such as the treatment program 40 (FIG. 5), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

While the invention has been primarily shown and described in conjunction with illuminating an area and/or treating a substance with ultraviolet radiation, it is understood that embodiments of the invention can be utilized in conjunction with generating other types of light and/or other applications. For example, an embodiment of the invention, such as the system shown in FIGS. 2A and 2B, can be directed to generating visible and/or infrared light to illuminate a region and/or a substance located within the region. In this case, a lighting system can use a combination of one or more solid state light sources and one or more lamps to generate the visible and/or infrared light having a predetermined minimum light intensity as described herein. Such illumination can be used for any of various applications, including general lighting (indoor or outdoor), surgical lighting, surveillance lighting, and/or the like.

As used herein, unless otherwise noted, the term "set" means one or more (i.e., at least one) and the phrase "any solution" means any now known or later developed solution. The singular forms "a," "an," and "the" include the plural forms as well, unless the context clearly indicates otherwise. Additionally, the terms "comprises," "includes," "has," and related forms of each, when used in this specification, specify the presence of stated features, but do not preclude the presence or addition of one or more other features and/or groups thereof. Additionally, spatially relative terms, such as "on," "below," "above," etc., may be used in reference to the orientation shown in the drawings. It is understood that embodiments of the invention are not limited to any particular orientation of a device described herein.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
a set of ultraviolet transparent windows defining at least a portion of at least one side of a treatment region;
a set of solid state ultraviolet sources configured to emit ultraviolet light directed through an ultraviolet transparent window of the set of ultraviolet transparent windows into the treatment region;
a set of ultraviolet lamps configured to emit ultraviolet light directed through an ultraviolet transparent window of the set of ultraviolet transparent windows into the treatment region; and
a control component configured to individually operate the set of solid state ultraviolet sources and the set of ultraviolet lamps to treat a substance located within the treatment region by illuminating the treatment region with ultraviolet radiation having a predetermined minimum ultraviolet intensity, wherein the control component illuminates the treatment region by concurrently turning on the set of solid state ultraviolet sources and the set of ultraviolet lamps and reducing power to the set of solid state ultraviolet sources over time in response to the set of ultraviolet lamps emitting a higher intensity of ultraviolet radiation.

2. The system of claim 1, wherein the ultraviolet light emitted by the set of solid state ultraviolet sources and the set of ultraviolet lamps is directed through the same ultraviolet transparent window.

3. The system of claim 1, wherein the ultraviolet light emitted by the set of solid state ultraviolet sources and the set of ultraviolet lamps is directed through different ultraviolet transparent windows in the set of ultraviolet transparent windows.

4. The system of claim 1, wherein the set of ultraviolet transparent windows define at least a portion of at least two sides of a channel, wherein the substance comprises a fluid flowing through the channel.

5. The system of claim 4, wherein the control component is configured to determine the predetermined minimum ultraviolet intensity based on a transparency of the fluid and a flow rate of the fluid.

6. The system of claim 1, wherein the predetermined minimum ultraviolet intensity is based on a level of contamination of the substance.

7. The system of claim 1, wherein the substance comprises a surface of an object.

8. The system of claim 1, wherein the set of solid state ultraviolet sources, the set of ultraviolet lamps, and the control component are mounted to a substrate.

9. The system of claim 1, wherein the control component pulses power to the set of solid state ultraviolet sources.

10. A system comprising:
    a set of ultraviolet transparent windows defining at least a portion of at least one side of a treatment region;
    a plurality of solid state ultraviolet sources configured to emit ultraviolet light directed through an ultraviolet transparent window of the set of ultraviolet transparent windows into the treatment region;
    an ultraviolet lamp configured to emit ultraviolet light directed through an ultraviolet transparent window of the set of ultraviolet transparent windows into the treatment region; and
    a control component configured to individually operate the plurality of solid state ultraviolet sources and the ultraviolet lamp to treat a substance located within the treatment region by illuminating the treatment region with ultraviolet radiation having a predetermined minimum ultraviolet intensity, wherein the control component illuminates the treatment region by concurrently turning on at least some of the plurality of solid state ultraviolet sources and the ultraviolet lamp and reducing power to the at least some of the plurality of solid state ultraviolet sources over time in response to the ultraviolet lamp emitting a higher intensity of ultraviolet radiation.

11. The system of claim 10, wherein the plurality of solid state ultraviolet sources includes a first subset of ultraviolet sources that emit UV-C ultraviolet radiation and a second subset of ultraviolet source that emit at least one of: UV-A ultraviolet radiation or blue UV radiation.

12. The system of claim 10, wherein the set of ultraviolet transparent windows are configured to diffusively transmit the ultraviolet radiation into the treatment region.

13. The system of claim 10, wherein the control component is configured to selectively operate a subset of the plurality of solid state ultraviolet sources based on a target contaminant.

14. The system of claim 10, further comprising a set of ultraviolet sensors located within the treatment region, wherein the control component adjusts operation of the at least some of the plurality of solid state ultraviolet sources based on the ultraviolet intensity data acquired by the set of ultraviolet sensors.

15. A lighting system comprising:
    a set of transparent windows defining at least a portion of at least one side of an illumination region;
    a plurality of solid state light sources configured to emit light directed through a transparent window of the set of transparent windows into the illumination region;
    a lamp configured to emit light directed through a transparent window of the set of transparent windows into the illumination region;
    a set of light sensors located within the illumination region; and
    a control component configured to individually operate the plurality of solid state light sources and the lamp to illuminate the illumination region with light having a predetermined minimum light intensity, wherein the control component adjusts operation of the at least some of the plurality of solid state light sources based on light intensity data acquired by the set of light sensors.

16. The lighting system of claim 15, wherein the light comprises ultraviolet radiation.

17. The lighting system of claim 15, wherein the control component is configured to determine the predetermined minimum light intensity based on a transparency of a substance located within the illumination region.

18. The lighting system of claim 15, wherein, in response to receiving a request to illuminate the illumination region, the control component concurrently turns on at least some of the plurality of solid state light sources and the lamp and reduces power to the at least some of the plurality of solid state light sources over time in response to the lamp emitting a higher intensity of light.

19. The lighting system of claim 15, wherein the predetermined minimum light intensity is based on a level of contamination of a substance located within the illumination region.

20. The lighting system of claim 16, wherein the control component is configured to determine the level of contamination of the substance based on the light intensity data acquired by the set of light sensors.

* * * * *